United States Patent [19]

Tenczar

[11] 4,030,494
[45] June 21, 1977

[54] FLUID CONNECTORS

[76] Inventor: Francis Tenczar, 8931 S. Bell, Chicago, Ill. 60620

[22] Filed: Nov. 15, 1976

[21] Appl. No.: 741,630

Related U.S. Application Data

[62] Division of Ser. No. 412,553, Nov. 5, 1973.

[52] U.S. Cl. .............................. 128/214 R; 83/171; 83/651.1; 285/3; 285/21; 285/423
[51] Int. Cl.[2] .................... A61M 5/00; F16L 47/00
[58] Field of Search ......... 285/3, 4, 2, 21, DIG. 16, 285/331, 363, DIG. 2, 423; 21/54 R, 102 R; 83/171, 170, 651.1; 128/272, 214 R, 214.2

[56] References Cited

UNITED STATES PATENTS

| 2,122,368 | 6/1938 | Engler | 83/171 X |
| 3,075,573 | 1/1963 | Piazze | 83/171 X |
| 3,202,442 | 8/1965 | Abbey et al. | 285/3 |
| 3,306,563 | 2/1967 | Soto | 128/272 X |
| 3,436,171 | 4/1969 | Weichselbaum et al. | 21/54 R X |
| 3,865,411 | 2/1975 | Rowe et al. | 285/363 |
| 3,902,489 | 9/1975 | Carter | 285/3 X |

FOREIGN PATENTS OR APPLICATIONS

| 1,300,635 | 8/1969 | Germany | 285/3 |
| 801,162 | 9/1958 | United Kingdom | 285/3 |

Primary Examiner—Thomas F. Callaghan
Attorney, Agent, or Firm—Dominik, Knechtel, Godula & Demeur

[57] ABSTRACT

A connector means for conveying fluid from a supply source to a delivery location, said connectors having one conduit extending to the supply source and another conduit extending to the delivery location. Each terminal part has a cylindrical housing with a closed end to which the conduit is joined, and having an opposite operable end which is closed by a penetrable barrier. The barrier and closed end of the housing define an interior environment safe from external contaminants. A male tubular coupler is in one housing, a female tubular coupler is in the other housing, and a penetrator element is disposed around one of the tubular connectors. The penetrable barriers have a film of covered adhesive. The exposed adhesive films are placed in face to face contact to coaxially align the housing parts and bond the barrier membranes to exclude the environment. The penetrator element pierces the adhering barriers by either moving the penetrator element from one housing into the coaxially aligned housing, or by telescoping the housing cylinders so that the adhering barriers are contacted by the fixed penetrator element. The male tubular connector then engages the female tubular connector within a protected environment to effect connection between the supply source and the delivery location.

6 Claims, 18 Drawing Figures

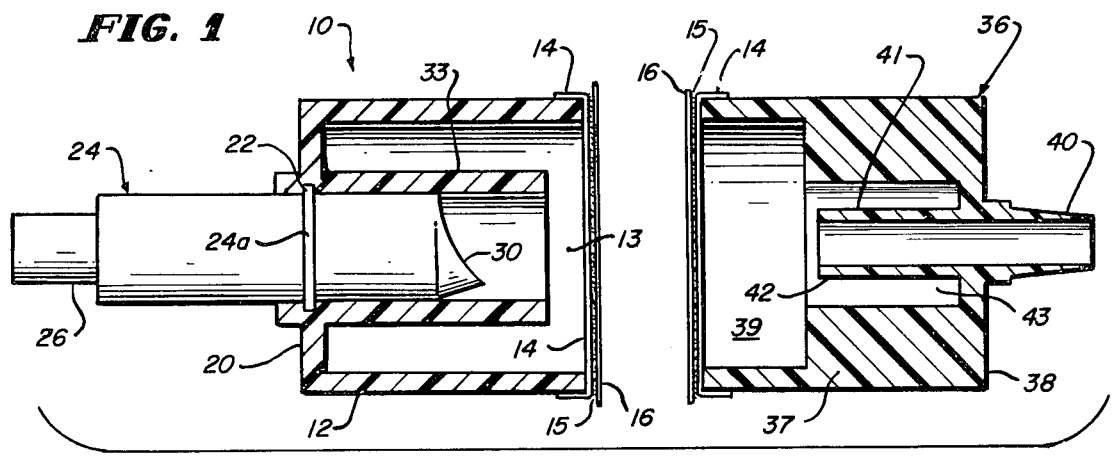
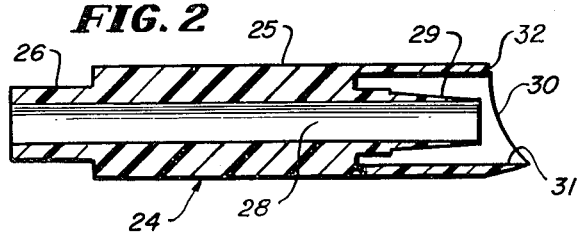
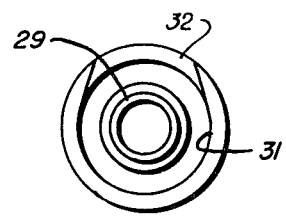
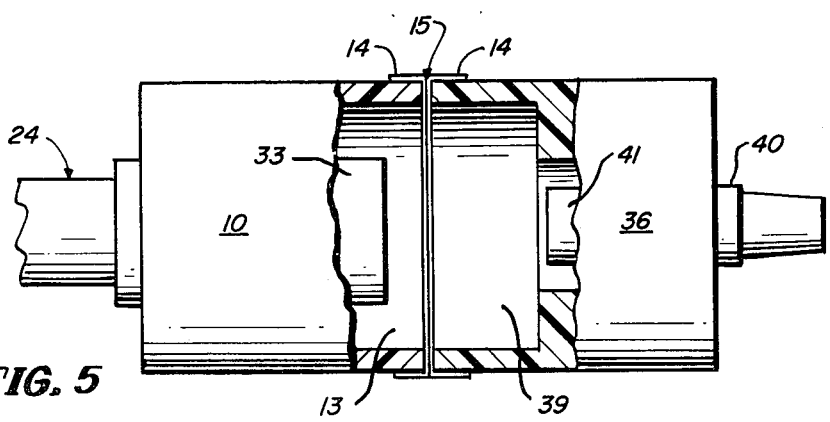
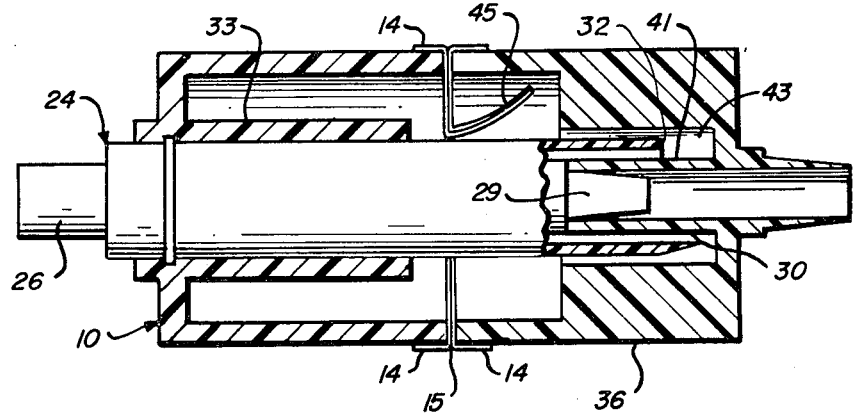
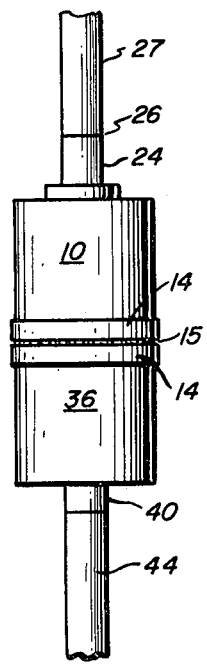

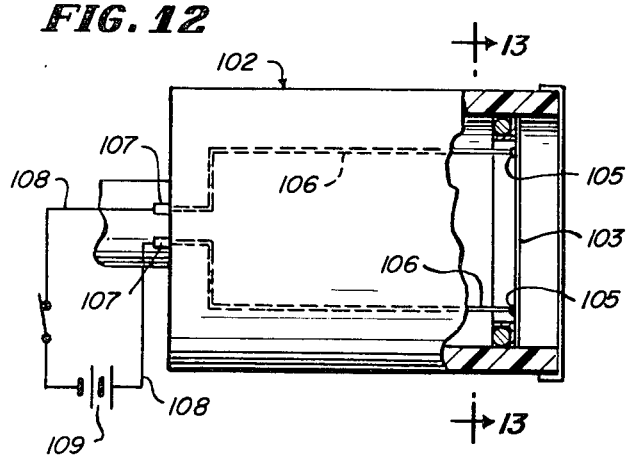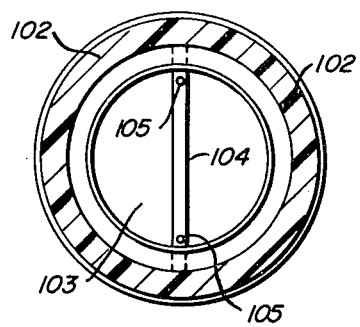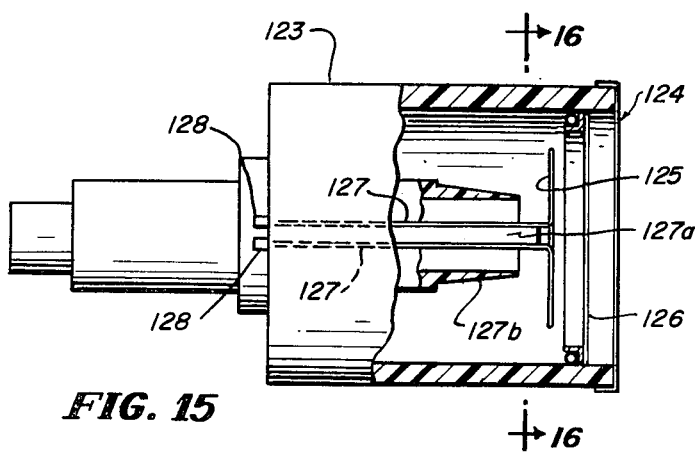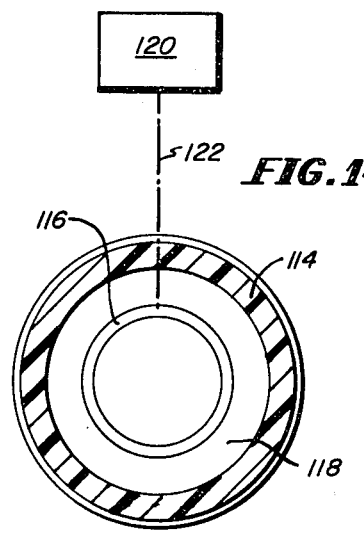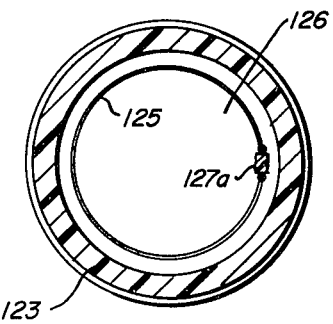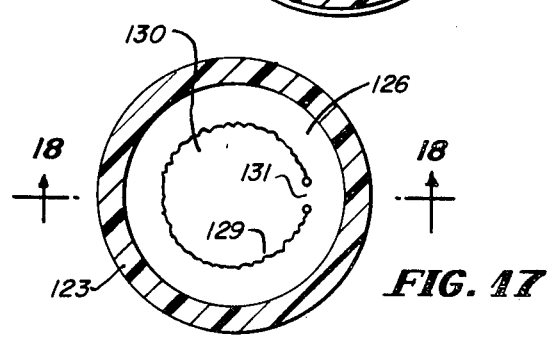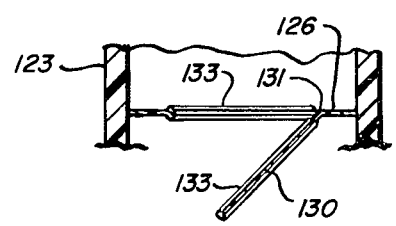

FLUID CONNECTORS

This is a division of application Ser. No. 412,553, filed Nov. 5, 1973.

This invention relates to an improved connector assembly, and particularly relates to a sterile connector assembly for blood bags or the like.

Connectors have been provided in the art for moving fluid under sterile conditions from a source to a delivered location, such as plastic blood bags. Such connectors are conventionally sterilized with a protective cover in place. When this cover is removed, the connector itself is exposed to the possibility of environmental (usually atmospheric) contamination in the time before the actual connection is frequently made with plastic bags for blood infusion and/or component preparation. Multiple transfers involving several bags and many different solutions increase the problem in procedures such as glyceralization, deglyceralization, and washing in the preparation of frozen red cells. Each manipulation of an exposed connector increases the likelihood of microbiological contamination. A connector that is manipulated while exposed to atmospheric contamination presents a serious problem to the practitioner and recipient. Although such exposed connectors may be rapidly connected to reduce the hazard of possible contamination such components have only a short useful time (now 24 hours) because of this danger of contamination. It will be appreciated that it is highly desirable to obtain a connection which can be made without loss of sterility. Reliably sterile connections would reduce wasteage of blood and components by increasing the safe time for use (expiration date) and encouraging component preparation.

It is known in the art that there exist additives which extend the preservation of red cells beyond the present allowable period of 21 days provided by conventional refrigeration. Such additives must, of course, be introduced from a supply source to the red cells, whole blood or component, without the danger of contamination. This necessitates a connection which assures protection from contamination. This goal is more reliably reached by providing a connector assembly in which the parts and elements that directly participate in the connection are maintained in a sterile environment throughout the actual connection. Connections may be desirable in other industrial applications which should be free from exterior contaminants, although sterility is not required. The term "contaminants" will collectively refer to the undesired presence of microorganisms, particulate matter, gas, and the like.

One object of the present invention is to provide an improved connector assembly allowing the connector parts to be engaged without exposure to environmental contamination. The actual connection should be made reliably, quickly and efficiently by relatively simple component parts which are economically manufactured.

Another object of the present invention is to provide a connector assembly in which sterile coupler elements are protected within internally sterile housings covered by penetrable barriers, having sterile adhesive film with removable covers so that only the adhesive film is momentarily exposed to possible atmospheric contamination and not the coupling means with the housings.

Yet another important object of the present invention is an improved sterile connector assembly in which a coupling connection with sterile parts is made only after penetrable barriers on each housing part are adhesively joined to properly align the housing parts.

Yet still another object of the present invention is an improved sterile connector assembly in which a sterile penetrator element is moved inside one sterile environment through penetrable barriers joined by an adhesive, and then moved into an adjoining sterile environment so that a coupling element in one sterile environment can engage a coupling element in another sterile environment.

Still another object of the present invention is an improved sterile connector assembly wherein housing parts containing sterile environments are telescopically engaged so that adhesively bonded penetrable barriers are moved against a fixed penetrator element to communicate previously isolated sterile environments.

Yet another object of the present invention is an improved sterile connector assembly in which telescoping housing parts provide positive alignment of coupling elements in respective housing parts following penetration through adhesively bonded penetrable barriers.

Yet still another object of the present invention is an improved sterile connector assembly in which penetrable barriers have dome-like configurations so that the high points are first bonded and the low points are last to be bonded to facilitate uniform adhesion of barriers with minimal entrapment of air and/or ambient environmental contaminants.

The foregoing objects and advantages are now attained together with other objects and advantages which will occur to practitioners upon considering the invention shown in the following disclosure, including drawings wherein:

FIG. 1 is a side elevational view, mostly in section, of a non-telescoping connection assembly;

FIG. 2 is a sectional view of the penetrator showing a male coupler, not shown as such in the view of FIG. 1;

FIG. 3 is an end view of the penetrator and coupling elements shown in FIG. 2;

FIG. 4 is a side elevational view of the connector assembly on a reduced scale, rotated 90° relative to the orientation shown in FIG. 1;

FIG. 5 is a side elevational view of the assembly shown in the view of FIG. 4, with cutaway portions, showing the joined connector parts prior to coupling engagement;

FIG. 6 is a view similar to that of FIG. 5, but mostly in section, showing coupling engagement of the connector;

FIG. 12 is a schematic side elevational view, partly in section, showing a conductive element heated by a source of power to sterilize penetrable portions of a barrier assembly;

FIG. 13 is a sectional view along line 13-13 of FIG. 12;

FIG. 14 is a highly schematic front elevational view of an alternative embodiment having a conductive element on a barrier which is energized without physical connection;

FIG. 15 is a side elevational view, partly in section, of an alternative embodiment wherein a conductive element cuts and seals the edges of adjacent barriers;

FIG. 16 is a sectional view taken along line 16-16 of FIG. 15;

FIG. 17 is a front sectional view showing the configuration of the cut barriers; and FIG. 18 is a sectional view taken along line 18-18 of FIG. 17, showing the cut barriers displaced as a flap.

Figure 7:
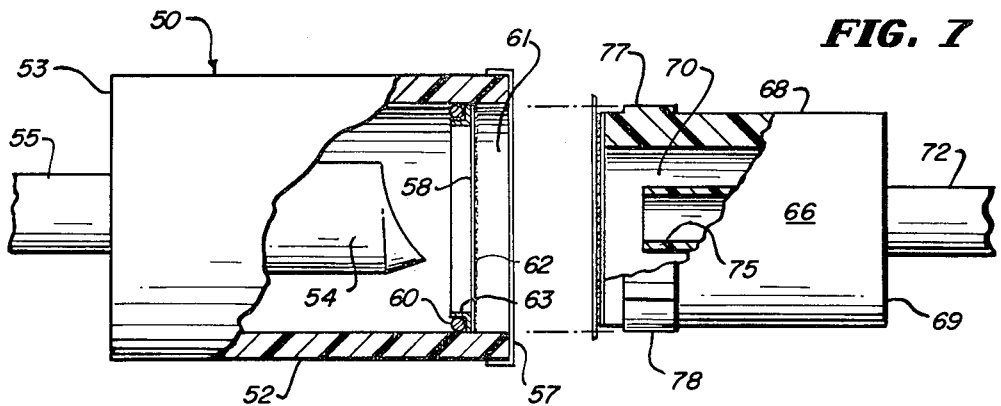
FIG. 7 is a side elevational view, partly in section, of an alternative embodiment of a telescoping connector assembly.

Looking at the views of FIGS. 1-6, there is shown a connector assembly including two terminal parts which are connected in an improved manner to prevent entry of contaminants during connection. A male connector terminal, shown generally as 10, is seen as having a cylindrical housing 12 with an openable end 13, covered by a penetrable barrier 14. The outside of the barrier has an adhesive film 15 which may be pressure sensitive or which may be applied just prior to joining the male and female terminals. A removable cover 16 is provided to cover the film when it is pressure sensitive or the like. The opposite end of the male terminal is closed at 20, and such closed end has an opening 22 which closely receives a movable penetrator and coupling assembly shown generally as 24, including sealing O-ring 24a. Economies and advantages of plastic molding may be utilized to form the penetrator and coupling element as an integral unit having an elongated body portion 25 with a conduit and/or fitting 26 for connection to a conduit 27 which leads to either a supply source or a delivery location. A central passageway 28 in the movable assembly continues to the end of a male coupler element 29. A penetrating end 30 is in advance of the male coupler element 29 to protect this coupler from contact with other elements of the assembly during connection with a female terminal coupler, as will be later described. The penetrator end may be provided with a piercing and pushing structure as shown in greater detail in the view of FIG. 3. A leading edge portion 31 is located in the semicircular area of the penetrator end; and a trailing pushing portion 32 is located in the upper semicircular area. The movable assembly 24 travels through a tubular support housing 33 which is shown as being integrally molded with the cylindrical housing 12 and closed end 20 of the terminal.

A female connector terminal is shown generally as 36, and such terminal includes a housing 37 having a closed end 38 and an opposite openable end 39. The openable end is closed by a barrier assembly which is similar to that described in association with male connector terminal 10. A conduit end or portion 40 extends outside of the terminal and communicates with the inside of the housing 37. The inside of the housing is shown with an inwardly extending and circular body part 41 which is concentrically positioned to tubular female coupler element 42. An annular spacing or gap 43 is between the body part 41 and the female coupler 42, and such gap accommodates the penetrator during coupling. A conduit 44, which may be flexible tubing, conveys fluid from a supply source or to a delivery location, depending on hookup.

In operation, the covers 16 are removed from the barrier assemblies to expose the pressure sensitive adhesive films 15. The terminals are then aligned and the barriers 14 are placed in face to face relationship by pressing the adhesive covered barriers together. In the alternative, the covers 16 can have pressure sensitive adhesive so they can be secured to the barriers and later removed. Sterile adhesive, or adhesive having anti-microbiologic agents, or both, can then be applied to the barrier faces prior to joining them so the terminals may be coaxially aligned.

The movable assembly 24 is then advanced in tubular support housing 33 until the pentrating end 30 pierces the bonded barrier assemblies. The cutting edge 31 pierces the adjoined and bonded barriers to begin formation of a flap 45 which is pushed out of the way with the help of pushing edge 32. The tubular end of the movable assembly engages the annular gap 43, and the male coupler 29 engages female coupler 42. The interlocking relationship of support housing 41 and the tubular end of the movable penetrator assembly 33, as well as the coupling engagement, assures secure and reliable coupling engagement.

Figure 8:
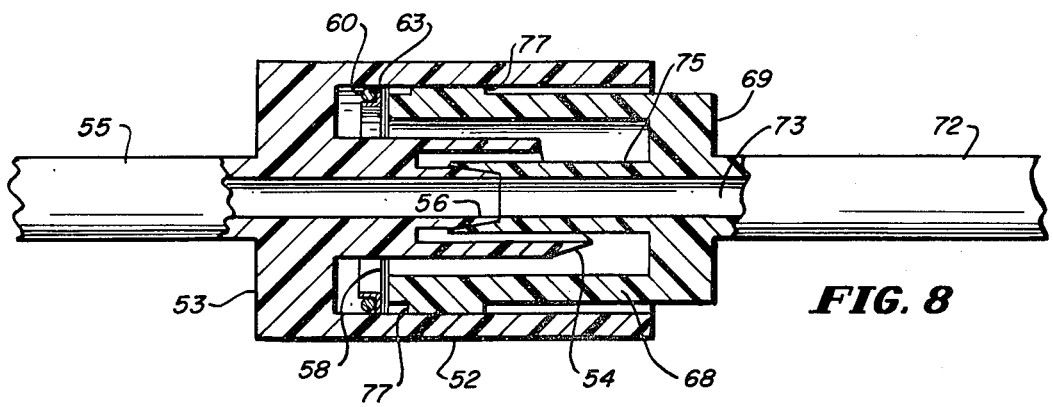
FIG. 8 is a sectional view of the terminal parts shown in the view of FIG. 7, but in coupling engagement.

An alternative embodiment for connecting the terminals is shown in the views of FIGS. 7 and 8. A male terminal connector shown generally as 50 includes a housing 52, a closed end 53 and an openable end 61. A conduit end 55 is integrally molded with the closed end 53. The male connector terminal illustrated herein is provided with a stationary coupler and penetrator assembly which includes housing 52, tubular penetrating end 54 of a configuration similar to that previously described, and a male coupler element 56, which is tapered for enhanced coupling engagement. The openable end 61 of the male connector terminal is provided with a removable cover 57. A barrier assembly is recessed relative to the openable end and is positioned adjacent the end of the penetrator. The cover 57 prevents entry of contaminates into the housing between the barrier assembly and the openable end. The assembly includes a penetrable barrier 58 which is held to the inside of the cylindrical housing by O-ring 60. An adhesive film 62 is provided on the face of the barrier. A substantially rigid pusher ring 63 supports the O ring and the barrier. The barrier assembly is movable against the penetrator 54, as will be later described.

The female connector terminal 66 includes housing 68, as closed end 69, and an openable end 70. The openable end is closed by a barrier assembly similar to that depicted in the views of the earlier described embodiment. A conduit 72 is at the closed end for connection to flexible tubing or the like, and such conduit communicates with the interior of the housing through passageway 73. A female coupler element 75 is wihin housing 68 and is continuous with conduit end 72 and coaxial with the male coupler 56. The outside of housing 68 is provided with an annular enlargement or spacer 77 which is provided with a plurality of grooved air passageways 78 which connect the opposite sides of the annular spacer.

In operation, the cover 57 is removed from the male terminal and the cover is likewise removed from the female terminal. The female connector terminal is then moved into telescoping engagement within the male connector terminal. The annular spacer 77 engages the inside of the cylindrical housing 52 in the male coupler terminal, and the air passages 78, in the form of grooves, allow escape of compressed air. This embodiment assures positive alignment and engagement of the male and female coupler elements. The membrane in the female terminal adheres to the barrier membrane recessed in the male terminal, and the bonded membranes, aided by pusher ring 63 and seal 60, are moved against the penetrator end 54.

Figure 9:
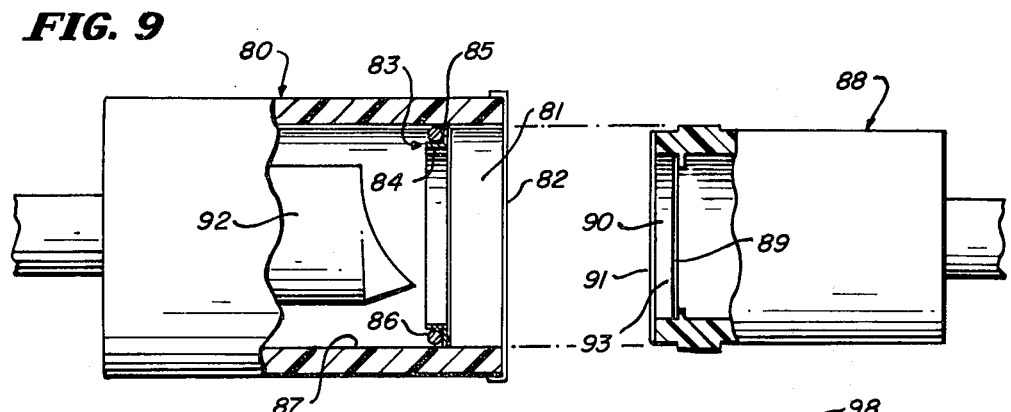
FIG. 9 is a side elevational view, partly in section, of an alternative embodiment showing plural barrier assemblies.

FIG. 9 shows an alternative embodiment wherein male connector terminal 80 has a barrier assembly recessed relative to openable end 81 closed by cover 82. The illustrated barrier assembly has a substantially rigid ring 83 of angular cross section having an axial arm 84 and a radial arm 85. The terms "axial" and "radial" are used relative to the center of the ring structure 83. An O-ring is inside the angle and sealingly contacts the cylindrical interior 87 of the terminal housing. A female terminal connector 88 is also provided with a recessed barrier assembly 89 shown with a barrier 89 mounted to fixed means. The openable end 90 of the female connector terminal has a penetrable barrier 91 which has a removable cover, not shown in this view. Cover 82 is removed from the male connector terminal and the female connector terminal is then telescopically engaged with the male connector terminal. Barrier 91 is then adhered to the penetrable barrier of the recessed barrier assembly in the male connector terminal. Adhesive may be present on either or both of these penetrable barriers. Continued movement of the female connector terminal will advance the bonded barrier assemblies against the stationary penetrator element 92. Such penetrating end will cut and move a bonded flap portion (not shown) into the space or gap 93 which is located between the bonded barriers and the penetrable barrier 89 in the female connector terminal 88. Continued movement of the female connector terminal will then result in the penetrator element 92 penetrating recessed barrier 89 and engaging the coupling elements in the respective terminal connectors. The bonded edge of the flap will be captured in the space 93 to isolate any possible contamination of the exposed edge of the flap.

Figure 10:
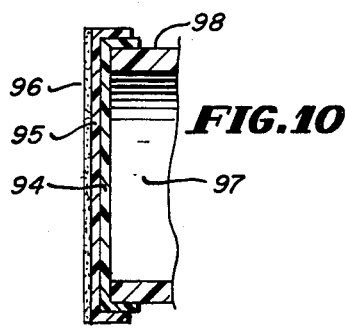
FIG. 10 is a portional and schematic sectional view on a highly enlarged scale of an alternative barrier assembly in a laminated structure.

A barrier assembly may be in the form of a laminated structure as shown in the portional, enlarged view of FIG. 10. The illustrated assembly includes an inner elastic barrier 94 which may be latex rubber. A substantially inelastic barrier 95, such as aluminum foil, freely abuts against elastic barrier 94 in unsecured relationship. An adhesive film 96 is shown as an outer layer relative to the openable end 97 of a terminal connector 98. The cover for the adhesive film is not shown in position, but it would cover the adhesive film in the usual way prior to connecting the terminals. A penetrator element will move through the substantially inelastic barrier 95 to form a flap, and such penetrator element will then stretch the elastic barrier 94. The cut passageway in the elastic barrier 94 will closely form around the periphery of the penetrator element. The elastic barrier will be pulled away from the inelastic barrier as the penetrator continues to advance. The formed gap between the barriers will then capture and isolate the flap.

Figure 11:
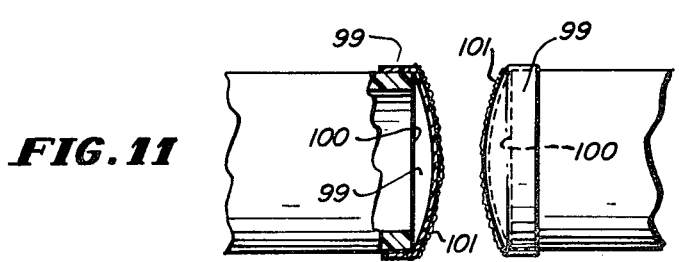
FIG. 11 is a schematic side view showing terminal connectors with a dome-shaped barriers to enhance prevention of contaminant entrapment when effecting adhesion of the barriers.

If desired, one or both barriers of the respective terminals may have dome-shaped configurations, that is, face to face convexity, as shown in the view of FIG. 11. The convex configuration of the barriers 99 may be preset by slightly increasing the thickness of the central portions. Such convex barriers are mounted to cover the openable ends 100 of the terminals. The schematic illustration relates to the embodiments of FIG. 1, but it may be utilized with the other illustrated embodiments. The adhesive film 101 on the convex barriers is provided to join the barriers with the high points of the dome making initial contact. Continued movement of the terminals toward each other will result in gradually increased surface area contact until the terminal portions are finally joined together, that is, the low points of the convex barriers. This gradual pushing outwardly prevents entrapment of contaminants between the barriers.

The embodiments shown in the views of FIGS. 12–18 illustrate means for sterilizing at least portions of the interface between the bonded barriers in the joined terminal connectors. Such means provide coupling a source of power to a conductive element associated with the barrier for a time and at an intensity level sufficient to elevate temperatures to sterilize at least portions of the bonded barrier through which the penetrator element will move. The exposed peripheral edge of the barrier flap will therefore be free of contamination which at least has the possiblity of occuring before the adhesive films of the barrier assemblies are contacted.

The embodiment of FIGS. 12 and 13 shows a housing similar to that illustrated in the views of FIGS. 7 and 8. A housing 102 has a barrier assembly which includes a barrier 103. A fusible element 104 is mounted to the barrier 103, and the fusible element is shown extending along a diameter of the barrier. A pair of diametrically opposed contacts 105 are positioned on the fusible element. Leads 106 extend from the contacts rearwardly to terminals 107 positioned on the closed end of the housing.

Conductors 108 join the terminals 107 to a power source shown as a voltage source 109. Desired voltage is applied for the fusing element 104 by conventional means, in the maner of a short circuit. The element 104 will fuse at temperatures sufficient to sterilize portions of the barrier 103 which will be contacted by the penetrator element. In the preferred embodiment, the voltage source and conductor circuit will be removable connected to terminals 107. The fusible element may be viewed as a fusible link in series with the electrical circuit which link is shortened or disrupted when the circuit is energized after being coupled with the voltage source. The membrane, in selected embodiments, may have sufficient portions disentegrated by the fused link so that coupling means or a penetrator may pass therethrough without cutting action.

The view of FIG. 14 illustrates a power source energizng barrier means, which may be the barrier itself or a conductive element. Such energization can be accomplished without physical connection between the power source and the terminal connector. A housing 114 may be the type shown in the views of FIGS. 7 and 8. A conductive element 116 may be present and may be in the shape of the illustrated ring, which is centrally mounted to a membrane 118. The ring may be aluminum metal foil, for example.

In one form, a power source 120 may be a radio frequency or R.F. transmitter which emits waves along path 122 toward conducive element 116 to induce an electrical current therein. Electric current is induced for a time sufficient to raise the temperature of the conductive element so that contacting membrane portions are heat sterilized and/or destroyed by ring 116.

Power source 120 may be an ultrasonic generator, and the generated ultrasonic waves can operate as known bacteriocidal means. Electrical induction may be provided in a ferro-magnetic ring, for example, the power source being means to induce electric current in the material.

The views of FIGS. 15–18 relate to an embodiment wherein a power source (not shown) is physically connected to a conductive element. A terminal connector 123 is shown with a recessed barrier assembly 124. The illustrated form resembles the embodiments of telescoping terminals as shown in the views of FIGS. 7 and 8.

An electrical resistance heating loop 125 may be used in place of a penetrator which cuts the barrier. The loop is positioned adjacent a penetrable barrier 126 which is plastic or other material that can be cut by a heated element, and then be heat-sealed by said heating element. The resistance heating element may be nichrome wire. Conductors 127 join the loop 125 to terminals 128 shown positioned at the closed end of the terminal connector 123. The conductors are supported on an elongated member 127a which extends beyond the end of male coupling element 127b. Barrier assemblies are placed in face to face contact as before, preferably with adhesive film, although such an adhesive film may be not present in some applications. A voltage source is then connected to the terminals 128 for a time sufficient to heat the loop element 125. Relative movement between adjoined barriers and the heating loop cuts the heat-disintegrable barriers and, at the same time, fuses the cut edges to form a sealing bead. The view of FIG. 17 shows the configuration of the heat cut in the adjoined, heat-disintegrable barriers. Such configuration is defined by a heat cut line 129 which follows the configuration of the heating loop 125. The heat-cut portion includes a central circular portion 130 and a hinge portion 131. The cut portion is moved or displaced by the elongated member or penetrator 127a supporting the leads 127. A sealing bead 133 fuses the cut edges of the adjoining barriers to fuse such barriers together and to sterilize the cut edges. Likelihood of contamination between the faces of the joined barriers is therefore eliminated by the heated, discontinuous loop which cuts, sterilizes, and fuses the edges of the formed flap and the remaining portions of the adjoined plastic barriers.

The heating element may be a part of the barrier by embedding or the like. The heating element may also be a part of a plastic insert which is positioned between the barriers prior to joining the barriers in face to face relationship. In both embodiments leads from the heating element extend to terminals for coupling to a power source. Such terminals may be part of the insert or otherwise.

The barriers referred to in the foregoing disclosure may be of various types. It is only required that such barriers be penetrated, pierced or cut by the penetrator element. It is preferred that such barriers allow a flap to be separated from the barrier material upon penetration by the cutting or penetrating end of the element. Examples of operable barriers are metal foil such as aluminum foil, or plastic. It is also possible for the barrier material to be elastomeric. The mechanical penetrating end pierces such an elastomeric material, and its memory and elasticity will form a closely adhering passageway for the cutting element. Such barriers may also comprise various and multiple plastic materials which are differently rigid or elastomeric.

The barriers may be variously mounted to close the openable end of the terminals. The barriers will extend to the continuous edge which defines the open edge of the terminals. The barriers may be coincidental with such continuous edge in one form or may overlap the continuous edge. The recessed barrier assembly has been illustrated as including an annular pusher element supporting the barrier and the O-ring holding the barrier assembly to the inside cylindrical wall. The particular orientation of these components may be changed or one annular spacer element may be provided which both holds the barrier to the inside cylindrical wall and supports it during movement.

Various adhesvie materials may be selected for the barriers depending on the barrier material and the sterilizing procedure, if any. It will be appreciated that temperature stable adhesives are required if applied before sterilizing procedures such as autoclaving. As mentioned, various anti-microbiological agents may be distributed in the adhesive material. Where the adhesive material is applied just prior to engaging the terminals it is preferred that such barriers still be covered to protect the exterior surfaces from contaminants, whether they be microorganisms or particulate matter. Where the barrier assembly is recessed, a cover will be mounted to close the openable end. The mounting may be simply effected by pressure-sensitive bonding materials or the like.

The claims of the invention are now presented and such terms may be better understood by reference to the language of the preceding specification and the views of the drawings.

What is claimed is:

1. A connector assembly to prevent entry of contaminants, including
    a pair of terminal connectors, each terminal connector having a housing, a conduit extending from one end of each housing and communicating with the interior of the housing, an openable end of each housing closed by a heat penetratable and fusible plastic barrier,
    coupling means within each housing communicating with the conduit,
    a penetrator element associated with one of the coupling means, and
    a conductive heating element positioned at least adjacent one barrier, and conductor means joining said heating element and said coupling means, whereby said plastic barriers may be adjoined and a power source may energize the element to penetrate the adjoined plastic barrier and, at the same time, fuse and sterilize the penetrated portions, whereby relative movement between adjoined plastic barriers and the penetrator element allows the coupling means to be joined.

2. A connector assembly as in claim 1 wherein said conductive heating element is a discontinuous loop and whereby relative movement between the adjoined barriers and the penetrator element pushes away a flap formed by the discontinuous loop heating element.

3. A connector assembly which includes the features of claim 1, and which further includes a film of adhesive substantially covering the area of at least one of the barriers.

4. A connector assembly as in claim 1 wherein said conductive heating element is an electrical resistant discontinuous loop, and said power source is an external voltage source, whereby relative movement between the adjoined barriers and the penetrator element pushes away a flap formed by the discontinuous loop penetrating and fusing the adjoined barriers.

5. A connector assembly which includes the features of claim 1 wherein the power source is an external ultrasonic generator.

6. A connector assembly which includes the features of claim 1 wherein the conductive element is a ferromagnetic material, and the power source is means for inducing an electric current in said conductive element.

* * * * *